United States Patent [19]

Kleiner

[11] Patent Number: 4,656,293

[45] Date of Patent: Apr. 7, 1987

[54] PROCESS FOR PREPARING ORGANIC CHLOROPHOSPHANES

[75] Inventor: Hans-Jerg Kleiner, Kronberg, Fed. Rep. of Germany

[73] Assignee: Hoechst Aktiengesellschaft, Frankfurt am Main, Fed. Rep. of Germany

[21] Appl. No.: 817,180

[22] Filed: Jan. 9, 1986

Related U.S. Application Data

[63] Continuation of Ser. No. 670,149, Nov. 9, 1984, abandoned.

[30] Foreign Application Priority Data

Nov. 12, 1983 [DE] Fed. Rep. of Germany ....... 3340995

[51] Int. Cl.$^4$ ..................... C07D 333/00; C07F 9/02
[52] U.S. Cl. ........................................... 549/6; 568/16
[58] Field of Search ............................... 568/16; 549/6

[56] References Cited

U.S. PATENT DOCUMENTS 2,871,263  1/1959  Short ................................... 568/16

FOREIGN PATENT DOCUMENTS 3313921 10/1984 Fed. Rep. of Germany .
362026  8/1984 U.S.S.R. .

OTHER PUBLICATIONS

Houben-Weyl, "Organische Phosphorverbindungen I" 4. Auflage, 1982, Georg Thieme Verlag Stuttgart, New York, Band El, Seiten 250, 283.

Houben-Weyl, "Methoden der Organischen Chemie", 4. Auflage; Band XII/1, 1963 Georg Thieme Verlag, Stuttgart, Seiten 202, 307.

Bulletin of Academy of Sciences of USSR, Band 28, Nr. 2, Teil 2, Feb. 1979, New York, USA; E. N. Tsvetkov et al. "New Reactions Involving Phosphorus–Phosphorus Bond Cleavage in Tetraalkyldiphosiphine Disulfides", Seite 396.

Primary Examiner—Alan Siegel
Attorney, Agent, or Firm—Curtis, Morris & Safford

[57] ABSTRACT

Organic chlorophosphanes of the formula III

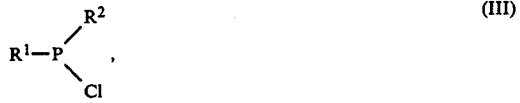

(III)

in which
$R^1$ is chlorine or an aliphatic radical, preferably only chlorine, and
$R^2$ is an aromatic, heterocyclic or aliphatic radical, are prepared by reacting organic phosphorus oxychlorides of the formula I

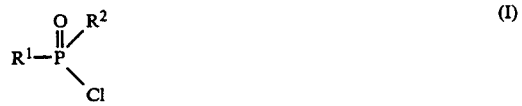

(I)

in which
$R^1$ is chlorine or an aliphatic radical, preferably only chlorine,
$R^2$ is an aromatic or heterocyclic radical in the event that $R^1$ is chlorine and an aromatic, heterocyclic or aliphatic radical in the event that $R^1$ is an aliphatic radical, with a trialkylphosphane of the formula II

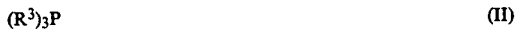

$(R^3)_3P$ (II)

in which $R^3$ is an aliphatic radical, at temperatures between about 20° and about 170° C. Said organic chlorophosphanes III are mainly intermediates in various fields, such as pharmaceuticals, plant protection, dyestuffs and polymers.

6 Claims, No Drawings

PROCESS FOR PREPARING ORGANIC CHLOROPHOSPHANES

This application is a continuation of application Ser. No. 670,149, filed Nov. 9, 1984 (now abandoned).

Organic chlorophosphanes are compounds of the general formulae $$R-P\begin{matrix}Cl\\ \\Cl\end{matrix} \quad \text{and} \quad R-P\begin{matrix}R\\ \\Cl\end{matrix}$$

in which R is an organic radical.

They are chiefly used as intermediates in various fields, such as pharmaceuticals, plant protection, dyestuffs and polymers.

They can be prepared by a number of different methods. In particular, aliphatic chlorophosphanes, especially methyldichlorophosphane, can be prepared, for example, by the method described in Soviet Union Originator Certificate No. 362,026; said method comprises reacting (deoxygenating) methylphosphonoyl dichloride with an aliphatic phosphane—specific examples mentioned being tri-n-butylphosphane(n-C$_4$H$_9$)$_3$ P and triisoamyl-phosphane(i-C$_5$H$_{11}$)$_3$P—in a molar ratio of 1:1 at temperatures between 175° and 220° C. The reaction is based on the following equation:

$$CH_3-P\begin{matrix}O\\ \\Cl\end{matrix}\begin{matrix}Cl\\ \\ \end{matrix} + R'_3P \longrightarrow CH_3-P\begin{matrix}Cl\\ \\Cl\end{matrix} + R'_3P=O$$

| Methyl-<br>phosphonoyl<br>dichloride | Trialkyl-<br>phosphane | Methyl-<br>dichloro-<br>phosphane | Trialkyl-<br>phosphane<br>oxide |

(R′ = aliphatic radical).

The yields are said to be about 60% of theory in respect of methyldichlorophosphane and between about 80 and 90% of theory in respect of the trialkylphosphane oxide.

It has also already been proposed in copending Ser. No. 599,539 (Patent Application P 33 13 921.0—HOE 83/F 060) to replace the trialkylphosphane in the reaction described in said Soviet Union Orginator Certificate by (aromatic) triphenylphosphane(C$_6$H$_5$)$_3$P. However, the yields of alkyldichlorophosphane which are obtained in this proposal are below 30% of theory and hence do not meet practical requirements. However, high chlorophosphane yields (usually between about 75 and 100% of theory) are obtained using the process of Patent Application P 33 13 921.0 when the starting material is not an aliphatic phosphonoyl dichloride (as in the process of the abovementioned Soviet Union Orginator Certificate), but an organic phosphorus oxychloride of the formula $$R''-P\begin{matrix}O\\ \\Cl\end{matrix}\begin{matrix}R'''\\ \\ \end{matrix}$$

in which
R″ is an aromatic or heterocyclic radical and
R‴ is an aliphatic radical or chlorine,
which is reacted with triphenylphosphane. The temperatures for this reaction are advantageously between about 100° and about 350° C., preferably between 170° and 250° C.

In the course of further development work on the reaction of phosphonoyl and phosphinoyl chlorides with organic phosphanes it has now been found that aromatic and heterocyclic phosphonoyl chlorides and aromatic-aliphatic, heterocyclic-aliphatic and pure aliphatic phosphinoyl chlorides can be reacted with aliphatic phosphanes at temperatures below those given in Soviet Union Originator Certificate No. 362,026 to form the desired chlorophosphanes (and phosphane oxides) in high yields.

Accordingly, the invention provides a process for preparing organic chlorophosphanes by reacting organic phosphorus oxychlorides with an organic phosphane at elevated temperatures, which comprises using as the organic phosphorus oxychlorides compounds of the formula I $$R^1-P\begin{matrix}O\\ \\Cl\end{matrix}\begin{matrix}R^2\\ \\ \end{matrix} \qquad (I)$$

in which
R$^1$ is chlorine or an aliphatic radical, preferably only chlorine, and
R$^2$ is an aromatic or heterocyclic radical in the event that R$^1$ is chlorine and is an aromatic, heterocyclic or aliphatic radical in the event that R$^1$ is an aliphatic radical, and as the organic phosphane a trialkylphosphane of the formula II $$(R^3)_3P \qquad (II)$$

in which R$^3$ is an aliphatic radical.

The temperatures for this reaction are generally between about 20° and about 170° C., preferably between about 60° and about 150° C., in particular between about 80° and about 130° C.

This reaction produces aromatic and heterocyclic dichlorophosphanes and aromatic-aliphatic, heterocyclic-aliphatic and pure aliphatic monochlorophosphanes in yields which are always between about 70 and 100% of theory, in accordance with the reaction equation:

$$R^1-P\begin{matrix}O\\ \\Cl\end{matrix}\begin{matrix}R^2\\ \\ \end{matrix} + (R^3)_3P \longrightarrow R^1-P\begin{matrix}R^2\\ \\Cl\end{matrix} + (R^3)_3P=O$$

| (I) | (II) | Chloro-<br>phosphane<br>(III) | Trialkyl-<br>phosphane<br>oxide<br>(IV) |

The successful outcome and the smooth course of this reaction within the specified temperature range were extremely surprising, since the reaction of purely aliphatic phosphonoyl dichlorides with aliphatic phosphanes at the elevated temperatures (175° to 220° C.) of the process in Soviet Union Orginator Certificate No. 362,026 produces lower (only about 60%) alkyldichlorophosphane yields.

The starting materials for the process according to the invention are compounds of the formulae I and II.

In the formula I, $R^1$ is chlorine or an aliphatic radical, preferably only chlorine. An aliphatic radical $R^1$ is preferably a $C_1$-$C_6$-alkyl radical, in particular a $CH_3$ or $C_2H_5$ radical.

In the event that $R^1$ is chlorine, $R^2$ is an aromatic or heterocyclic radical, and in the event that $R^1$ is an aliphatic radical, $R^2$ is an aromatic, heterocyclic or aliphatic radical.

The aromatic or heterocyclic radical is preferably a phenyl or thienyl radical which can be substituted by inert groups. Inert groups are groups which do not react in the course of the reaction taking place here. Preferred inert groups of this type are here alkyl groups and halogenoalkyl and halogen groups, in particular $C_1$-$C_6$-alkyl groups (especially $CH_3$ and $C_2H_5$), $CF_3$ and chlorine. Both the phenyl radical and the thienyl radical can be monosubstituted or polysubstituted; preferably, the phenyl is monosubstituted or disubstituted and the thienyl radical is unsubstituted.

An aliphatic radical $R^2$ can, in principle, be the same as an $R^1$ radical and is likewise preferably a $C_1$-$C_6$-alkyl radical (in particular $CH_3$ and $C_2H_5$).

If in the formula I $R^1$ is chlorine, the compounds are aromatic and heterocyclic phosphonoyl dichlorides, such as, for example, phenylphosphonoyl dichloride, tolylphosphonoyl dichlorides, xylylphosphonoyl dichlorides, 3-trifluoromethylphenylphosphonoyl dichloride, 4-chlorophenylphosphonoyl dichloride, thienylphosphonoyl dichloride and so on. The compounds are prepared by known methods. For instance, phenylphosphonoyl dichloride $C_6H_5P(O)Cl_2$, for example, can be obtained inter alia, by phosgenating phenylphosphonic acid diesters $C_6H_5P(O)(OR)_2$, in which R is an organic radical; phenylphosphonic acid diesters in turn can be obtained, for example, by reacting bromobenzene with trialkyl phosphites in the presence of nickel bromide.

If $R^1$ is an aliphatic radical, the compounds of the formula I are aromatic-aliphatic, heterocyclic-aliphatic or purely aliphatic phosphinoyl chlorides, such as, for example, phenylmethylphosphinoyl chloride, tolylmethylphosphinoyl chloride, phenylethylphosphinoyl chloride, thienylmethylphosphinoyl chloride, dimethylphosphinoyl chloride, ethylmethylphosphinoyl chloride, methylpropylphosphinoyl chloride, diethylphosphinoyl chloride and so on. These compounds are likewise accessible by known methods.

In the trialkylphosphanes of the formula II, the aliphatic radical $R^3$ is preferably an alkyl radical of up to 10 carbon atoms, in particular of 4 to 8 carbon atoms. Examples of trialkylphosphanes of the formula II are triethylphosphane, tributylphosphane, trihexylphosphane and trioctylphosphane.

The organic phosphorus oxychlorides of the formula I and the trialkylphosphane of the formula II are normally used in the (stoichiometric) molar ratio of 1:1. However, other molar ratios are also conceivable. For instance, it is also possible to use said trialkylphosphane II in excess; this excess then is not converted during the reaction. The presence of inert solvents and diluents is possible, but in general affords no particular advantage.

The reaction is normally carried out under atmospheric pressure; however, the use of superatmospheric pressure is possible and in certain cases can be advisable.

To carry out the reaction, organic phosphorus oxychlorides I are mixed with trialkylphosphane II in an inert gas atmosphere (for example nitrogen). It can be advisable to blend the components together slowly if the reaction is exothermic. After the components have been mixed, the mixture, still in the inert gas atmosphere, is held at the reaction temperature for a certain period; this reaction period lasts on average about 1 to 10 hours.

After the reaction has ended, chlorophosphanes III which have formed, i.e. dichlorophosphanes (from phosphonoyl dichlorides I) or monochlorophosphanes (from phosphinoyl chlorides I), are advantageously recovered by distillation and hence separated from trialkylphosphane oxides IV. Said crude trialkylphosphane oxides IV can be likewise isolated by distillation. As the chlorophosphanes III which are formed are of interest virtually only as intermediates, they can, if desired, also be directly processed further in the reaction mixture obtained at the end of the reaction.

For example, said reaction mixtures of aromatic dichlorophosphanes (in the formula III $R^1$ is chlorine and $R^2$ is an aromatic radical) and trialkylphosphane oxide IV can be added dropwise at about 90° C. to excess water, producing the aromatic phosphonous acids

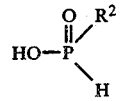

($R^2$ is an aromatic radical) which form a phase together with trialkylphosphane oxide IV, while the aqueous phase contains the bulk of the hydrogen chloride formed. After this phase has been removed, the organic phase is neutralized with aqueous sodium hydroxide solution. In this way the sodium salt of the phosphonous acid is obtained in the form of an aqueous solution and trialkylphosphane oxide IV is obtained in the organic phase.

The process according to the invention produces chlorophosphanes having an aromatic or heterocyclic plus, if desired, an aliphatic radical bonded to the phosphorus from organic phosphorus oxychlorides through reaction with an aliphatic phosphane in (compared with the process of Soviet Union Originator Certificate No. 362,062) consistently higher yields at lower temperatures. For this reason the invention can be said to be a further development which advances the art.

The following examples will explain the invention in more detail.

EXAMPLE 1

50 g (0.257 mole) of phenylphosphonoyl dichloride are added dropwise with stirring and in a nitrogen atmosphere to 95 g (0.257 mole) of trioctylphosphane, the temperature rising to 50° C. The mixture is then held at 100° C. for 1 hour and is then distilled. 32 g of dichlorophenylphosphane (which corresponds to yields of 70% of theory) pass over at 75° C. under 0.43 kPa and 89 g of trioctylphosphane oxide (which corresponds to a yield of 90% of theory) pass over at 220° C. under 0.067 kPa.

EXAMPLE 2

48.3 g (0.248 mole) of phenylphosphonoyl dichloride are added dropwise with stirring and in a nitrogen atmosphere to 50 g (0.248 mole) of tributylphosphane in the course of 45 minutes. The temperature rises to 40° C. The mixture is then briefly heated to 100° C. and is subsequently distilled. This produces 32 g of dichlorophenlphosphane (73% of theory) and, at 0.027 kPa and a transition temperature of 115° C., 47.5 g of tributylphosphane oxide (which corresponds to yields of 90% of theory).

EXAMPLE 3

40 g (0.175 mole) of p-chlorophenylphosphonoyl dichloride are rapidly added dropwise with stirring and in a nitrogen atmosphere to 64.5 g (0.175 mole) of trioctylphosphane. The temperature rises to 60° C. The mixture is then held at 100° C. for one hour. After the batch has cooled down, 45 ml of methylene chloride are added. The mixture is stirred and filtered with suction to remove 3 g of solids. The filtrate is freed of methylene chloride in vacuo and under about 0.1333 kPa is distilled up to an internal temperature of 240° C. This produces 30 g of p-chlorophenyldichlorophosphane. That corresponds to a yield of 84% of theory. The residue is distilled at 0.067 kPa and the transition temperature of 220° C. This produces about 63 g of pure trioctylphosphane oxide (melting point: 47°-50° C.) (about 95% of theory).

EXAMPLE 4

84.5 g (0.228 mole) of trioctylphosphane and 43 g (0.228 mole) of methyl-p-tolylphosphinoyl chloride are mixed with stirring in a nitrogen atmosphere. The mixture separates into two phases and is then heated with stirring. The reaction mixture becomes homogeneous at 110° C. It is then held at 130° C. for 5 hours. 31.5 g of chloromethyl-p-tolylphosphane are then distilled off at 0.053 kPa and a transition temperature of 70° C. The residue solidifies and constitutes crude trioctylphosphane oxide. The yield is 80% of theory.

EXAMPLE 5

24.4 g (0.117 mole) of p-tolylphosphonoyl dichloride are rapidly added dropwise with stirring and in a nitrogen atmosphere to 52 g (0.141 mole) of trioctylphosphane, the temperature rising to 50° C. The mixture is then heated to 100° C. and is held at that temperature for 30 minutes with stirring. 18.5 g of dichloro-p-tolylphosphane (which corresponds to a yield of 82% of theory) are then distilled off at about 0.08 kPa and a transition temperature of 70° C. The residue constitutes a crude mixture of trioctylphosphane and trioctylphosphane oxide.

EXAMPLE 6

147 g (0.396 mole) of trioctylphosphane and 50 g (0.396 mole) of ethylmethylphosphinoyl chloride are mixed with stirring in a nitrogen atmosphere. The mixture is then held at 150° C. for 8 hours. 27 g of chloroethylmethylphosphane are then distilled off at 50° C. and about 0.4 kPa and are condensed in a cold trap downstream of the distillation apparatus. 20 g of ethylmethylphosphinoyl chloride are then distilled off at 0.27 kPa and a transition temperature of about 70° C. While the conversion is 60% of theory the yield of chloroethylmethylphosphane is 85% of theory.

The residue solidifies and constitutes crude trioctylphosphane oxide.

I claim:

1. A process for preparing an organic chlorophosphane, which consists essentially of reacting, at a temperature of from about 60° to about 150° C., an organic phosphorus oxychloride of the formula I

in which
R¹ is chlorine or an aliphatic radical, and
R² is an aromatic or heterocyclic radical, with a trialkylphosphane of the formula II

in which R³ is an aliphatic radical.

2. A process as claimed in claim 1, wherein the aliphatic radical R¹ contains from 1 to 6 carbon atoms, the aromatic or heterocyclic radical R² is a phenyl or thienyl radical or said radical substituted by at least one inert group, and R³ is an aliphatic radical of up to 10 carbon atoms.

3. A process as claimed in claim 1, wherein R¹ is chlorine.

4. A process as claimed in claim 3, wherein the temperature is from about 80° to about 130° C.

5. A process as claimed in claim 1, wherein the aliphatic radical R¹ is methyl or ethyl.

6. A process as claimed in claim 1, wherein R³ is alkyl of from 4 to 8 carbon atoms.

* * * * *